United States Patent [19]

Trinh et al.

[11] Patent Number: 5,660,845

[45] Date of Patent: *Aug. 26, 1997

[54] SOLID CONSUMER PRODUCT COMPOSITIONS CONTAINING SMALL PARTICLE CYCLODEXTRIN COMPLEXES

[75] Inventors: Toan Trinh, Maineville; John Michael Gardlik, Cincinnati, both of Ohio

[73] Assignee: The Procter & Gamble Company, Cincinnati, Ohio

[*] Notice: The term of this patent shall not extend beyond the expiration date of Pat. No. 5,543,157.

[21] Appl. No.: 658,329

[22] Filed: Jun. 5, 1996

Related U.S. Application Data

[62] Division of Ser. No. 477,338, Jun. 7, 1995, Pat. No. 5,543,157, which is a division of Ser. No. 268,157, Jun. 29, 1994, Pat. No. 5,552,378, which is a continuation of Ser. No. 707,266, May 24, 1991, abandoned, which is a continuation of Ser. No. 486,757, Mar. 6, 1990, abandoned.

[51] Int. Cl.$^6$ .................................................... A61K 9/62
[52] U.S. Cl. ........................ 424/418; 424/461; 424/493; 536/103
[58] Field of Search .................................. 424/493, 418, 424/461; 530/103

[56] References Cited

U.S. PATENT DOCUMENTS

| | | | |
|---|---|---|---|
| 4,024,223 | 5/1977 | Noda et al. | 424/180 |
| 4,365,061 | 12/1982 | Szejtli et al. | 436/103 |
| 4,438,106 | 3/1984 | Wagu et al. | 424/180 |
| 4,675,395 | 6/1987 | Fukayawa et al. | 536/103 |
| 4,732,759 | 3/1988 | Shibanai et al. | 424/94.61 |
| 5,543,157 | 8/1996 | Trinh et al. | 424/493 |

*Primary Examiner*—James H. Reamer
*Attorney, Agent, or Firm*—Robert B. Aylor

[57] ABSTRACT

An effective amount of active/cyclodextrin complex, in the form of particles having particle sizes below about 12 microns, is incorporated into solid consumer product compositions. The complexes provide fast release of the active when they are wetted even when the amount of water available to effect release of the active is limited as in personal use compositions like drugs, foods, and cosmetics where active release is typically effected by body fluids. Preferred actives include perfumes, flavors, and pharmaceutical materials that are used by consumers.

4 Claims, No Drawings

SOLID CONSUMER PRODUCT COMPOSITIONS CONTAINING SMALL PARTICLE CYCLODEXTRIN COMPLEXES

This is a division of application Ser. No. 08/477,338, filed on Jun. 7, 1995, now U.S. Pat. No. 5,543,157 which is a division of application Ser. No. 08/268,157, filed Jun. 29, 1994, now U.S. Pat. No. 5,552,378; which is a continuation of application Ser. No. 07/707,266, filed May 24, 1991, now abandoned; which is a continuation of application Ser. No. 07/486,757, filed Mar. 6, 1990, now abandoned.

TECHNICAL FIELD

The present invention relates to an improvement in solid consumer products (compositions) containing solid cyclodextrin inclusion complexes of actives, which are typically hydrophobic materials like perfumes, flavoring materials, pharmaceutical actives, antibacterials, bleaches, etc., said products, and/or compositions, being, preferably, either in particulate form; compounded with other materials in solid form, e.g., tablets, pellets, agglomerates, gel sticks, etc.; or attached to a substrate.

BACKGROUND OF THE INVENTION

The use of cyclodextrin as a complexing agent for materials is well documented, including the disclosures in U.S. Pat. No. : U.S. Pat. No. 4,348,416, Boden (flavoring material for use in chewing gum, dentifrices, cosmetics, etc.); U.S. Pat. No. 4,296,138, Boden (similar to U.S. Pat. No. 4,348,416); U.S. Pat. No. 4,265,779, Gandolfo et al. (suds suppressors for use in detergent compositions); U.S. Pat. No. 3,816,393, Hayashi et al. (prostaglandins for use as pharmaceuticals); U.S. Pat. No. 3,846,551, Mifune et al. (insecticidal and acaricidal compositions); U.S. Pat. No. 4,024,223, Noda et al. (menthol, methyl salicylate, etc.); U.S. Pat. No. 4,054,736, Hayashi et al. (similar to U.S. Pat. No. 3,816,393); U.S. Pat. No. 4,073,931, Akito et al. (nitroglycerin/cyclodextrin complexes); U.S. Pat. No. 4,228,160, Szjetli et al. (indomethacin); U.S. Pat. No. 4,247,535, Bernstein et al. (cyclodextrin complexes of complement inhibitors); U.S. Pat. No. 4,268,501, Kawamura et al. (cyclodextrin complexes of anti-asthmatic actives); U.S. Pat. No. 4,365,061, Szejtli et al. (strong inorganic oxyacids complexes); U.S. Pat. No. 4,371,673, Pitha (retinoids); U.S. Pat. No. 4,380,626, Szejtli et al. (hormonal plant growth regulator); U.S. Pat. No. 4,438,106, Wagu et al. (long chain fatty acids useful to reduce cholesterol); U.S. Pat. No. 4,474,822, Sato et al. (cyclodextrin/tea essence complexes); U.S. Pat. No. 4,529,608, Szejtli et al. (honey aroma); U.S. Pat. No. 4,547,365, Kubo et al. (cyclodextrin/hair-waving-active complexes); U.S. Pat. No. 4,548,811, Kubo et al. (waving lotion); U.S. Pat. No. 4,596,795, Pitha (sex hormones); U.S. Pat. No. 4,616,008, Hirai et al. (antibacterial complexes); U.S. Pat. No. 4,636,343, Shibanai (insecticide complexes); U.S. Pat. No. 4,663,316, Ninger et al. (antibiotics); U.S. Pat. No. 4,675,395, Fukazawa et al. (hinokitiol); U.S. Pat. Nos. 4,732,759 and 4,728,510, Shibanai et al. (complexes of bath additives); and U.S. Pat. No. 4,751,095, Karl et al. (aspartame/cyclodextrin complex), all of said patents being incorporated by reference. Despite the voluminous art relating to the preparation and use of cyclodextrin complexes in various products, there has been a continuing, but apparently unrecognized, need for improved release of the complexed actives, e.g., perfume, flavor, etc.

Cyclodextrin complexes of various actives have been disclosed as set forth in detail in the patents incorporated by reference herein. However, the patents do not reflect the commercial realities of preparing successful consumer products. It is not sufficient that an effect can be obtained by the use of large amounts of a material, or that the effect can be obtained occasionally. For commercial success, the effect must be obtained consistently and the cost must be commensurate with the benefit obtained. The previous lack of commercial use and/or success for complexes in consumer products is undoubtedly related to the excessive expense of such complexes and/or to the fact that using such complexes in large particle size results in insufficient release and/or speed of release. Given the need to maximize the protection of the active, it is not surprising that there has been no discussion of small particle size.

SUMMARY OF THE INVENTION

It has now been discovered that actives in cyclodextrin complexes incorporated into consumer compositions can be released much faster and more effectively by the action of water if the particle size of the complex, in an amount that provides at least an effective amount of said active, is reduced to less than about 12, preferably less than about 10, more preferably less than about 8, and even more preferably less than about 5, typically between about 0.001 and about 10, preferably between about 0.05 and about 5 microns (micrometers). The small particle complexes provide a remarkable and totally unexpected improvement in the speed of the release of the active when the complex is wetted. This improved speed of release was not expected in view of the voluminous art that discloses good release from the larger particles that typically result from the normal crystallization processes for preparing cyclodextrin complexes. Furthermore, the excellent stability of the small particle size complexes is not taught by any prior art.

The advantage of improved active release is especially important where the amount of water available for effecting release of the active is limited, e.g., as in consumer products for personal use, where release is effected by body fluids. Body fluids such as saliva, sweat, gastric juices, etc., already have considerable dissolved material present and there is a limited amount of body fluid so that the amount of water available to effect release is very limited.

For many personal use compositions such as drugs, foods, etc., the release of active should be as quick as possible. The improved speed of release in many instances is necessary to provide a concentration of the active that will provide the desired effect, and in other instances is necessary to avoid the use of excessive amounts of complex. When the amount or temperature of the water is low or the time available to effect release is limited, small particles are essential to provide any noticeable effect. For some uses, such as in, e.g., laundry detergents, the speed-of-release effect may not be noticed and, in fact, may not be desirable.

Processes for forming complexes of the actives with cyclodextrins and/or their derivatives are described in the patents incorporated hereinbefore and hereinafter. These complexes have been disclosed generically and have been suggested for use in a variety of products as discussed hereinbefore.

DESCRIPTION OF THE INVENTION

Cyclodextrin complexes can be readily prepared in small particle form by mechanically mixing the active ingredient with the cyclodextrin in the presence of water. In general, there is a disadvantage in using such methods since the completeness of the reaction forming the complex is usually lower than in crystallization processes and the level of active that can be carried by the complex is already low. Nonetheless, the improvement in release is sufficiently great to make use of the mechanical method desirable. One can also grind the larger particles, e.g., those made by crystallization processes to achieve the desired particle size. For any use that requires fast release, the particle size reduction is essential to see the full benefit of the active. For many actives, there is a critical level required to obtain a response. The art, in general, teaches that release is quick. In fact, the release of active from a cyclodextrin complex by the action of water is quite slow. Thus it is essential that at least an effective amount of the active be in small particle form. Effective amounts depend upon the active and the end result desired.

1. CYCLODEXTRINS

As used herein, the term "cyclodextrin" (CD) includes any of the known cyclodextrins such as unsubstituted cyclodextrins containing from six to twelve glucose units, especially, alpha-, beta-, gamma-cyclodextrins, and mixtures thereof, and/or their derivatives, and/or mixtures thereof, that are capable of forming inclusion complexes with perfume ingredients. Beta-cyclodextrin is the most preferred cyclodextrin and the one whose complex benefits most from the small particle size. Alpha-, beta-, and gamma-cyclodextrins can be obtained from, among others, American Maize-Products Company (Amaizo), Hammond, Ind.; Roquette Corporation, Gurnee, Ill.; and Chinoin Pharmaceutical and Chemical Works, Ltd., Budapest, Hungary. There are many derivatives of cyclodextrins that are known. Representative derivatives are those disclosed in U.S. Pat. No: 3,426,011, Parmerter et al., issued Feb. 4, 1969; U.S. Pat. Nos. 3,453,257, 3,453,258, 3,453,259, and 3,453,260, all in the names of Parmerter et al., and all issued Jul. 1, 1969; U.S. Pat. No. 3,459,731, Gramera et al., issued Aug. 5, 1969; U.S. Pat. No. 3,553,191, Parmerter et al., issued Jan. 5, 1971; U.S. Pat. No. 3,565,887, Parmerter et al., issued Feb. 23, 1971; U.S. Pat. No. 4,535,152, Szejtli et al., issued Aug. 13, 1985; U.S. Pat. No. 4,616,008, Hirai et al., issued Oct. 7, 1986; U.S. Pat. No. 4,638,058, Brandt et al., issued Jan. 20, 1987; U.S. Pat. No. 4,746,734, Tsuchiyama et al., issued May 24, 1988; and U.S. Pat. No. 4,678,598, Ogino et al., issued Jul. 7, 1987, all of said patents being incorporated herein by reference. Examples of cyclodextrin derivatives suitable for use herein are methyl-$\beta$-CD, hydroxyethyl-$\beta$-CD, and hydroxypropyl-$\beta$-CD of different degrees of substitution (DS), available from, among others, Aldrich Chemical Company, Milwaukee, Wis.; Wacker Chemicals (U.S.A.), New Canaan, Conn.; and Chinoin Pharmaceutical Works, Budapest, Hungary. Water-soluble derivatives are also highly desirable.

The individual cyclodextrins can also be linked together, e.g., using multifunctional agents to form oligomers, polymers, etc. Examples of such materials are available commercially from Amaizo and from Aldrich Chemical Company ($\beta$-CD/epichlorohydrin copolymers).

It is also desirable to use mixtures of cyclodextrins to provide a mixture of complexes. Such mixtures, e.g., can provide more even odor profiles by encapsulating a wider range of active ingredients and/or preventing reforming large crystals of said complexes. Mixtures of cyclodextrins can conveniently be obtained by using intermediate products from known processes for the preparation of cyclodextrins including those processes described in U.S. Pat. No. : 3,425,910, Armbruster et al., issued Feb. 4, 1969; U.S. Pat. No. 3,812,011, Okada et al., issued May 21, 1974; U.S. Pat. No. 4,317,881, Yagi et al., issued Mar. 2, 1982; U.S. Pat. No. 4,418,144, Okada et al., issued Nov. 29, 1983; and U.S. Pat. No. 4,738,923, Ammeraal, issued Apr. 19, 1988, all of said patents being incorporated herein by reference. Preferably at least a major portion of the cyclodextrins are alpha-cyclodextrin, beta-cyclodextrin, and/or gamma-cyclodextrin, more preferably beta-cyclodextrin. Some cyclodextrin mixtures are commercially available from, e.g., Ensuiko Sugar Refining Company, Yokohama, Japan.

2. THE ACTIVES

Many different active materials can be complexed with cyclodextrins as set out in the patents incorporated hereinbefore and hereinafter by reference. Perfumes ate a highly desirable active material that can usually benefit from protection and that can be complexed, especially when the perfume is relatively hydrophobic. Flavoring active materials are like perfumes in that they tend to be adversely affected by the environment and require protection. Another type of active material that is often complexed with cyclodextrins is a pharmaceutical active that needs to be protected from the environment. Yet another type of active material that is advantageously complexed is an oxidation or reduction active that interacts with other materials that are present. In general, active materials that form complexes with cyclodextrin and are released by the action of water are useful in the practice of this invention.

A. Perfumes

Detergents; fabric softening products; cosmetics, including antiperspirants, hair and skin care products; and disposable absorbent products like diapers and catamenial articles, all typically contain some perfume to provide some fragrance to provide an olfactory aesthetic benefit and/or to serve as a signal that the product is effective.

The perfume in such products is often lost before it is needed. Perfumes can be subject to damage and/or loss by the action of, e.g., oxygen, light, heat, etc. For example, due to the high energy input and large air flow in the drying process used in the typical automatic laundry dryers, a large part of the perfume provided by dryer-added softener products has been lost out the dryer vent. Even for less volatile components, as described hereinafter, only a small fraction remains on the fabrics after the drying cycle. The loss of the highly volatile fraction of the perfume, as described hereinafter, is much higher. Usually the loss of the highly volatile fraction is practically total. Due to this effect, many perfumes used in, e.g., dryer-added fabric softener compositions, have been composed mainly of less volatile, high boiling (having high boiling points), perfume components to maximize survival of the odor character during storage and use and thus provide better "substrate substantivity." The main function of a small fraction of the highly volatile, low boiling (having low boiling points), perfume components in these perfumes is to improve the fragrance odor of the product itself, rather than impacting on the subsequent substrate, e.g., fabric or body, odor. However, some of the volatile, low boiling perfume ingredients can provide a fresh and clean impression to the substrate, and it is highly desirable that these ingredients be deposited and present on the substrate.

Perfumes used in cosmetics and disposable absorbent products also tend to be lost prematurely. It is highly desirable to have volatile perfume ingredients available until they are released by water contained in, e.g., urine, sweat, menses, etc.

The perfume ingredients and compositions of this invention are the conventional ones known in the art. Selection of any perfume component, or amount of perfume, is based solely on aesthetic considerations. Suitable perfume compounds and compositions can be found in the art including U.S. Pat. No.: 4,145,184, Brain and Cummins, issued Mar. 20, 1979; U.S. Pat. No. 4,209,417, Whyte, issued Jun. 24, 1980; U.S. Pat. No. 4,515,705, Moeddel, issued May 7, 1985; and U.S. Pat. No. 4,152,272, Young, issued May 1, 1979, all of said patents being incorporated herein by reference. Many of the art recognized perfume compositions are relatively substantive, as described hereinafter, to maximize their odor effect on substrates. However, it is a special advantage of perfume delivery via the perfume/cyclodextrin complexes that nonsubstantive perfumes are also effective.

A substantive perfume is one that contains a sufficient percentage of substantive perfume materials so that when the perfume is used at normal levels in products, it deposits a desired odor on the treated substrate. In general, the degree of substantivity of a perfume is roughly proportional to the percentage of substantive perfume material used. Relatively substantive perfumes contain at least about 1%, preferably at least about 10%, substantive perfume materials.

Substantive perfume materials are those odorous compounds that deposit on substrates via the treatment process and are detectable by people with normal olfactory acuity. Such materials typically have vapor pressures lower than that of the average perfume material. Also, they typically have molecular weights of about 200 or above, and are detectable at levels below those of the average perfume material.

Perfumes can also be classified according to their volatility, as mentioned hereinbefore. The highly volatile, low boiling, perfume ingredients typically have boiling points of about 250° C. or lower. Many of the more moderately volatile perfume ingredients are also quickly lost. For example, substantially all of such perfumes are lost in the drying cycle of a typical laundry process. The moderately volatile perfume ingredients are those having boiling points of from about 250° C. to about 300° C. The less volatile, high boiling, perfume ingredients referred to hereinbefore are those having boiling points of about 300° C. or higher. A significant portion of even these high boiling perfume ingredients, considered to be highly substantive, can be lost, e.g., during a laundry drying cycle, and it is desirable to have means to retain more of these ingredients on the substrates. Many of the perfume and flavor ingredients as discussed hereinafter, along with their odor and/or flavor characters, and their physical and chemical properties, such as boiling point and molecular weight, are given in "Perfume and Flavor Chemicals (Aroma Chemicals)," Steffen Arctander, published by the author, 1969, incorporated herein by reference.

Examples of the highly volatile, low boiling, perfume ingredients are: anethole, benzaldehyde, benzyl acetate, benzyl alcohol, benzyl formate, iso-bornyl acetate, camphene, cis-citral (neral), citronellal, citronellol, citronellyl acetate, paracymene, decanal, dihydrolinalool, dihydromyrcenol, dimethyl phenyl carbinol, eucalyptol, geranial, geraniol, geranyl acetate, geranyl nitrile, cis-3-hexenyl acetate, hydroxycitronellal, d-limonene, linalool, linalool oxide, linalyl acetate, linalyl propionate, methyl anthranilate, alpha-methyl ionone, methyl nonyl acetaldehyde, methyl phenyl carbinyl acetate, laevo-menthyl acetate, menthone, iso-menthone, myrcene, myrcenyl acetate, myrcenol, nerol, neryl acetate, nonyl acetate, phenyl ethyl alcohol, alpha-pinene, beta-pinene, gamma-terpinene, alpha-terpineol, beta-terpineol, terpinyl acetate, and vertenex (para-tertiary-butyl cyclohexyl acetate). Some natural oils also contain large percentages of highly volatile perfume ingredients. For example, lavandin contains as major components: linalool; linalyl acetate; geraniol; and citronellol. Lemon oil and orange terpenes both contain about 95% of d-limonene.

Examples of moderately volatile perfume ingredients are: amyl cinnamic aldehyde, iso-amyl salicylate, beta-caryophyllene, cedrene, cinnamic alcohol, coumarin, dimethyl benzyl carbinyl acetate, ethyl vanillin, eugenol, iso-eugenol, flor acetate, heliotropine, 3-cis-hexenyl salicylate, hexyl salicylate, lilial (para-tertiarybutyl-alpha-methyl hydrocinnamic aldehyde), gamma-methyl ionone, nerolidol, patchouli alcohol, phenyl hexanol, beta-selinene, trichloromethyl phenyl carbinyl acetate, triethyl citrate, vanillin, and veratraldehyde. Cedarwood terpenes are composed mainly of alpha-cedrene, beta-cedrene, and other $C_{15}H_{24}$ sesquiterpenes.

Examples of the less volatile, high boiling, perfume ingredients are: benzophenone, benzyl salicylate, ethylene brassylate, galaxolide(1,3,4,6,7,8-hexahydro-4,6,6,7,8,8-hexamethyl-cyclopenta-gama-2-benzopyran), hexyl cinnamic aldehyde, lyral(4-(4-hydroxy-4-methyl pentyl)-3-cyclohexene-10-carboxaldehyde), methyl cedrylone, methyl dihydro jasmonate, methyl-beta-naphthyl ketone, musk indanone, musk ketone, musk tibetene, and phenylethyl phenyl acetate.

Cyclodextrin inclusion complexes (perfume/cyclodextrin, or perfume/CD, complexes), as described hereinafter, of the high boiling, the moderately volatile, and the low boiling perfume ingredients are stable (a) throughout the mixing of the complexes with the remainder of the compositions, e.g., the molten fabric softener mixes, especially when the fabric softener mixes contain some clay, and the coating of the resulting fabric softening compositions onto flexible substrates to form fabric conditioning sheets, (b) during the application of the composition to the substrate, e.g., during the drying of the wet fabrics in tumble dryers, and (c) during use, e.g., when the cosmetic is on the skin or during the wear of the dry fabrics. The content of the perfume in the complex is typically from about 5% to about 15%, more normally from about 7% to about 10%.

B. Flavors

Flavoring materials are desirable actives to use in the form of cyclodextrin complexes. As used herein, the term "flavors" also includes spices, flavor enhancers, etc., that contribute to the overall flavor perception. Advantages of cyclodextrin/flavor complexes include: (1) the protection of active ingredients from reactions induced by heat, light, and/or oxygen; (2) less loss of flavor by volatilization and/or sublimation; and (3) providing stable, standardized, powders that contain flavors to reduce packaging and/or labor costs. In the household, the flavoring materials can be stored longer and the measurement is more precise, since the flavor content remains more stable. At the same time, the natural material content of some flavors can be reduced to minimize the potential for allergic reactions and the risk of microbial contamination can be reduced. Minimization of preparation time is another benefit that is especially important. All of these benefits are also important to commercial food preparation. The reduction in food handling saves labor and minimizes the potential for contamination of the food.

The cyclodextrin/flavor complexes are readily prepared as discussed hereinafter, and the cyclodextrin complexes do not adversely affect the appearance, texture, and/or flavor of the food. The texture may, in some instances, be beneficially thickened, e.g., as in drinks and soups prepared from mixes. The flavor/cyclodextrin complexes lose very little of their flavor active content in storage. If stability in the presence of extreme heat is desired, the complexes can be coated with, e.g., hardened fat, polymers, etc.

The content of the flavor in the complex is typically from about 5% to about 15%, more often from about 7% to about 10%. Flavor actives, like perfume actives, normally consist of several components. While it is usually important to incorporate the active into the complex without changing the composition, it is also possible to complex only the more vulnerable components and thereby minimize the level of complex required.

Specific examples of flavors and flavor enhancers include those disclosed in U.S. Pat. No. 4,348,416, Boden, incorporated herein by reference. I.e., organic acids, e.g., acetic acid, formic acid, 2-hexenoic acid, benzoic acid, n-butyric acid, caproic acid, caprylic acid, cinnamic acid, isobutyric acid, isovaleric acid, alphamethylbutyric acid, propionic acid, valeric acid, 2-methyl-2-pentenoic acid and 2-methyl-3-pentenoic acid; ketones and aldehydes, e.g., 2-methyl-3-ketofuran, acetophenone, acetone, acetyl methyl carbinol, acrolein, n-butanal, crotonal, diacetyl, 2-methylbutanal, beta-beta-dimethyl acrolein, methyl n-amyl ketone, n-hexanal, 2-hexanal, isopentenal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl-furfural, cinnamaldehyde, beta-cyclohomocitral, 2-pentanone, 2-pentenal and propanal, alcohols such as 1-butanol, benzyl alcohol, iso-borneol, trans-2-buten-1-ol, ethanol, geraniol, 1-hexanol, 2-heptanol, trans-2-hexen-1-ol, cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, menthol, acetoin; esters such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, indecane, trimethylnaphthalene, undecane, caryophyllene, alphaphellandrene, beta-phellandrene, p-cymene, alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils and extracts such as jasmine absolute, cassia oil, cinnamon bark oil, black pepper oleoresin, tumeric oil, oil of black pepper, rose absolute, orris absolute, oil of cubeb, oil of coriander, oil of pimento leaf, oil of patchouli, oil of nutmeg, ginger oil, lemon essential oil, dill oil, lemon grass oil, oil of valerion, marjoram oil, raspberry oil, cinnamon oil, carrot oil, anise oil, orange oil, thyme oil, peppermint oil, sweet cumin oil, celery oil, garlic oil, onion oil, tarragon oil, caraway oil, basil oil, bay leaf oil, mustard oil, sage, tea extract, coffee extract, safran oil, Bulgarian rose, capsicum, yara yara, vanilla, nut oils and the synthetic versions of these natural oils and extracts; lactones such as $\gamma$-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperdine.

Specific examples of the invention include the use of the complexes in the preparation of powdered mixes, e.g., drink mixes. For example, tea extract, synthetic sweeteners, and/or one or more flavors such as bergamot, jasmine, lemon oil, peppermint oil, etc., can be added to a powdered instant tea mix and the resulting product has a more stable flavor profile and the flavor is released immediately to allow for full enjoyment of the flavor. Examples of tea mixtures and instant tea mixes can be found in U.S. Pat. No. 4,474,822, Sato et al., issued Oct. 2, 1984; and in Brit. Pat. 2,074,838, to Chinoin Gyogyszer, issued Nov. 11, 1981, said patents being incorporated herein by reference.

Similar advantages are found when a flavor ingredient such as a beef extract is complexed and added to a powdered soup mix. The advantage of the complex is especially apparent for those flavors that are prone to decomposition and/or require considerable time to prepare.

Dairy products are especially desirable to complex. Butter flavor is especially prone to destruction during storage. The use of complexes is especially desirable when refrigeration is not possible or is not dependable.

The use of complexes in "prepared foods" that are prepared and packaged and then sold after a period of time has elapsed, is especially advantageous. Uncomplexed flavor components are often changed after storage resulting in a "less fresh" flavor.

Complexed flavors are also very useful in other products like chewing gum, toothpastes and powders, medicines, etc., where the product is used in the mouth, but not for food.

C. Pharmaceuticals

Another class of actives that is highly desirable to complex is pharmaceutical materials (drugs). Drugs that have been suggested for complexation include those described in the patents incorporated by reference hereinbefore, and especially U.S. Pat. No. 4,727,064, Pitha, issued Feb. 23, 1988, incorporated herein by reference. The list includes ibuprofen, acetylsalicylic acid (or its salts), acetamidophen, apomorphine, butylated hydroxytoluene, chlorthalidone, cholecalciferol, dexamethasone, dicumarol, digoxin, diphenylhydantoin, estradiol, estriol, ethinylestradiol-3-methyl ether, ethisterone, furosemide, hydroflumethiazide, indomethacin, iproniazid phosphate, 17-methyltestosterone, nitroglycerin, norethindrone, oubain, oxprenolol, progesterone, retinal, trans-retinoic acid and/or its salts, retinol, spironolactone, sulpiride, testosterone, theophylline, aryclovir, cloridine HCl etc.

The complexation of drugs is highly desirable since loss of activity can mean the drug will be ineffective if the proper dose is not administered.

3. COMPLEX FORMATION

The complexes of this invention are formed in any of the ways known in the art. Typically, the complexes are formed either by bringing the perfume and the cyclodextrin together in a suitable solvent, e.g., water, or, preferably, by kneading the ingredients together in the presence of a suitable, preferably minimal, amount of solvent, preferably water. The kneading method is particularly desirable because it results in smaller particles so that there is less, or no, need to reduce the particle size and less solvent is needed and therefore less separation of the solvent is required. Suitable processes are disclosed in the patents incorporated hereinbefore by reference. Additional disclosures of complex formation can be found in Atwood, J. L., J. E. D. Davies & D. D. MacNichol, (Ed.): *Inclusion Compounds*, Vol. III., Academic Press (1984), especially Chapter 11, and Atwood, J. L. and J. E. D. Davies (Ed.): *Proceedings of the Second International Symposium of Cyclodextrins* Tokyo, Japan, (July, 1984), both of said publications being incorporated by reference.

In general, active/cyclodextrin complexes have a molar ratio of active compound to cyclodextrin of 1:1. However, the molar ratio can be either higher or lower, depending on the size of the active compound and the identity of the cyclodextrin compound. The molar ratio can be determined easily by forming a saturated solution of the cyclodextrin and adding the active to form the complex. In general the complex will precipitate readily. If not, the complex can usually be precipitated by the addition of electrolyte, change of pH, cooling, etc. The complex can then be analyzed to determine the ratio of active to cyclodextrin.

As stated hereinbefore, the actual complexes are determined by the size of the cavity in the cyclodextrin and the size of the active molecule. Although the normal complex is one molecule of active in one molecule of cyclodextrin, complexes can be formed between one molecule of active and two molecules of cyclodextrin when the active molecule is large and contains two portions that can fit in the cyclodextrin. Highly desirable complexes can be formed using mixtures of cyclodextrins since some actives like perfumes and flavor extracts are normally mixtures of materials that vary widely in size. It is usually desirable that at least a majority of the material be alpha-, beta-, and/or gamma-cyclodextrin, more preferably beta-cyclodextrin.

Processes for the production of cyclodextrins and complexes are described in U.S. Pat. No. : 3,812,011, Okada, Tsuyama, and Tsuyama, issued May 21, 1974; U.S. Pat. No. 4,317,881, Yagi, Kouno and Inui, issued Mar. 2, 1982; U.S. Pat. No. 4,418,144, Okada, Matsuzawa, Uezima, Nakakuki, and Horikoshi, issued Nov. 29, 1983; U.S. Pat. No. 4,378, 923, Ammeraal, issued Apr. 19, 1988, all of said patents being incorporated herein by reference. Materials obtained by any of these variations are acceptable for the purposes of this invention. It is also acceptable to initially isolate the inclusion complexes directly from the reaction mixture by crystallization.

Continuous operation usually involves the use of supersaturated solutions, and/or kneading, and/or temperature manipulation, e.g., heating and then either cooling, freeze-drying, etc. The complexes may be dried or not depending on the next step in the process for making the desired composition. In general, the fewest possible process steps are used to avoid loss of active.

4. COMPLEX PARTICLE SIZES

The particle sizes of the complexes herein are selected to improve the release, and especially the speed-of-release, of the active. The small particles of this invention, e.g., those having a particle size of less than about 12 microns, preferably less than about 10 microns, more preferably less than about 8 microns, and even more preferably less than about 5 microns, are desirable for providing a quick release of the active when the complexes are wetted.

The particle size range is typically between about 0.001 and 10 microns, preferably between about 0.05 and 5 microns. It is highly desirable that at least an effective amount of the active be in complexes having the said particle sizes. It is desirable that at least about 75%, preferably at least about 80% and more preferably at least about 90% of the complex that is present have the said particle sizes. It is even better if essentially all of the complex has the said particle sizes.

These small particles of the invention are conveniently prepared by kneading methods and/or grinding techniques. Cyclodextrin complexes with large particle sizes can be pulverized to obtain the desired smaller particles of about 10 microns and less by using, e.g., a fluid energy mill. Examples of fluid energy mills are the Trost Air Impact Pulverizers, sold by Gatlock Inc., Plastomer Products, Newtown, Pa.; the Micronizer fluid energy mills sold by Sturtevant, Inc., Boston, Mass.; and the Spiral Jet Mill sold by Alpine Division, MicroPul Corporation (Hosokawa Micron International, Inc., Summit, N.J.

As used herein, the particle size refers to the largest dimension of the particle and to the ultimate (or primary) particles. The size of these primary particles can be directly determined with optical or scanning electron microscopes. The slides must be carefully prepared so that each contains a representative sample of the bulk cyclodextrin complexes. The particles sizes can also be measured by any of the other well-known methods, e.g., wet sieving, sedimentation, light scattering, etc. A convenient instrument that can be used to determine the particle size distribution of the dry complex powder directly (without having to make a liquid suspension or dispersion) is the Malvern Particle and Droplet Sizer, Model 2600C, sold by Malvern Instruments, Inc., Southborough, Mass. Some caution should be observed in that some of the dry particles may remain agglomerated. The presence of agglomerates can be further determined by microscopic analysis. Some other suitable methods for particle size analysts are described in the article "Selecting a particle size analyzer: Factors to consider," by Michael Pohl, published in Powder and Bulk Engineering, Volume 4 (1990), pp. 26–29, incorporated herein by reference. It is recognized that the very small particles of the invention can readily aggregate to form loose agglomerates that are easily broken apart by either some mechanical action or by the action of water. Accordingly, particles should be measured after they are broken apart, e.g., by agitation or sonication. The method, of course, should be selected to accommodate the particle size and maintain the integrity of the complex particles, with iterative measurements being made if the original method selected proves to be inappropriate.

5. THE COMPOSITIONS

The present invention also relates to improved solid consumer compositions which are either (A) incorporated into articles of manufacture in which the compositions containing the complexes are, e.g., on a substrate, or, are (B) in the form of particles (including, where appropriate, agglomerates, pellets, and tablets of said particles).

A. Substrate Articles

In preferred embodiments, the present invention encompasses articles of manufacture. Representative articles are those that are adapted for use to provide unique perfume benefits and to soften fabrics in an automatic laundry dryer, of the types disclosed in U.S. Pat. Nos.: 3,989,631 Marsan, issued Nov. 2, 1976; U.S. Pat. No. 4,055,248, Marsan, issued Oct. 25, 1977; U.S. Pat. No. 4,073,996, Bedenk et al., issued Feb. 14, 1978; U.S. Pat. No. 4,022,938, Zaki et al., issued May 10, 1977; U.S. Pat. No. 4,764,289, Trinh, issued Aug. 16, 1988; U.S. Pat. No. 4,808,086, Evans et al., issued Feb. 28, 1989; U.S. Pat. No. 4,103,047, Zaki et al., issued Jul. 25, 1978; U.S. Pat. No. 3,736,668, Dillarstone, issued Jun. 5, 1973; U.S. Pat. No. 3,701,202, Compa et al., issued Oct. 31, 1972; U.S. Pat. No. 3,634,947, Furgal, issued Jan. 18, 1972; U.S. Pat. No. 3,633,538, Hoeflin, issued Jan. 11, 1972; and U.S. Pat. No. 3,435,537, Rumsey, issued Apr. 1, 1969; and U.S. Pat. No. 4,000,340, Murphy et al., issued Dec. 28, 1976, all of said patents being incorporated herein by reference.

Typical articles of manufacture of this type include articles comprising:

I. a fabric conditioning composition comprising:
 i. from about 30% to about 99% of fabric softening agent; and
 ii. an effective amount, preferably from about 0.5% to about 60%, of perfume/cyclodextrin complex, as described hereinafter;
II. a dispensing means which provides for release of an effective amount of said composition to fabrics in an automatic laundry dryer at automatic laundry dryer operating temperatures, e.g., from about 35° C. to 115° C.

When the dispensing means is a flexible substrate, e.g., in sheet configuration, the fabric conditioning composition is releasably affixed on the substrate to provide a weight ratio of conditioning composition to dry substrate ranging from about 10:1 to about 0.5:1, preferably from about 5:1 to about 1:1. The invention also comprises the method of manufacturing such an article of manufacture utilizing said complex ii., either by application of the complex ii. directly to said dispensing means II., or by premixing the complex ii. with the fabric softening agent i. The softener helps protect the complex from the water in the environment which is desirable. However, separate application of complex to said substrate is also possible and can diminish interaction of softener ingredients with the perfume.

The term "fabric softening agent" as used herein includes cationic and nonionic fabric softeners used alone and also in combination with each other. A preferred fabric softening agent of the present invention is a mixture of cationic and nonionic fabric softeners.

(1) Fabric Softening Agents

Examples of fabric softening agents that are especially useful in the substrate articles are the compositions described in U.S. Pat. No. 4,103,047, Zaki et al., issued Jul. 25, 1978; U.S. Pat. No. 4,237,155, Kardouche, issued Dec. 2, 1980; U.S. Pat. No. 3,686,025, Morton, issued Aug. 22, 1972; U.S. Pat. No. 3,849,435, Diery et al., issued Nov. 19, 1974; and U.S. Pat. No. 4,037,996, Bedenk, issued Feb. 14, 1978; said patents are hereby incorporated herein by reference.

Another preferred type of fabric softener is described in detail in U.S. Pat. No. 4,661,269, Toan Trinh, Errol H. Wahl, Donald M. Swartley and Ronald L. Hemingway, issued Apr. 28, 1987, said patent being incorporated herein by reference.

Examples of nonionic fabric softeners are the sorbitan esters, $C_{12}$–$C_{26}$ fatty alcohols, and fatty amines described herein.

More biodegradable fabric softener compounds can be desirable. Biodegradability can be increased, e.g., by incorporating easily destroyed linkages into hydrophobic groups. Such linkages include ester linkages, amide linkages, and linkages containing unsaturation and/or hydroxy groups. Examples of such fabric softeners can be found in U.S. Pat. No. : 3,408,361, Mannheimer, issued Oct. 29, 1968; U.S. Pat. No. 4,709,045, Kubo et al., issued Nov. 24, 1987; U.S. Pat. No. 4,233,451, Pracht et al., issued Nov. 11, 1980; U.S. Pat. No. 4,127,489, Pracht et al., issued Nov. 28, 1979; U.S. Pat. No. 3,689,424, Berg et al., issued Sep. 5, 1972; U.S. Pat. No. 4,128,485, Baumann et al., issued Dec. 5, 1978; U.S. Pat. No. 4,161,604, Elster et al., issued Jul. 17, 1979; U.S. Pat. No. 4,189,593, Wechsler et al., issued Feb. 19, 1980; and U.S. Pat. No. 4,339,391, Hoffman et al., issued Jul. 13, 1982, said patents being incorporated herein by reference.

A preferred article of the present invention includes a fabric treatment composition which comprises from about 0.5% to about 60%, preferably from about 1% to about 50%, more preferably from about 5% to about 40%, of perfume/cyclodextrin complex and from about 30% to about 99%, preferably from about 40% to about 90%, of fabric conditioning (softening) agent. Preferably, said fabric softening agent is selected from cationic and nonionic fabric softeners and mixtures thereof. Preferably, said fabric softening agent comprises a mixture of about 5% to about 80% of a cationic fabric softener and about 10% to about 85% of a nonionic fabric softener by weight of said fabric treatment composition. The selection of the components is such that the resulting fabric treatment composition has a melting point above about 38° C. and is flowable at dryer operating temperatures.

(2) Dispensing Means

In a preferred substrate article embodiment, the fabric treatment compositions are provided as an article of manufacture in combination with a dispensing means such as a flexible substrate which effectively releases the composition in an automatic laundry (clothes) dryer. Such dispensing means can be designed for single usage or for multiple uses. The dispensing means can also be a "carrier material" that releases the fabric softener composition and then is dispersed and/or exhausted from the dryer.

The dispensing means will normally carry an effective amount of fabric treatment composition. Such effective amount typically provides sufficient fabric conditioning agent and/or anionic polymeric soil release agent for at least one treatment of a minimum load in an automatic laundry dryer. Amounts of fabric treatment composition for multiple uses, e.g., up to about 30, can be used. Typical amounts for a single article can vary from about 0.25 g to about 100 g, preferably from about 0.5 g to about 10 g, most preferably from about 1 g to about 5 g.

One such article comprises a sponge material releasably enclosing enough fabric treatment composition to effectively impart fabric soil release and softness benefits during several cycles of clothes. This multi-use article can be made by filling a hollow sponge with about 20 grams of the fabric treatment composition.

Other devices and articles suitable for dispensing the fabric treatment composition into automatic dryers include those described in U.S. Pat. No. : 4,103,047, Zaki et al., issued Jul. 25, 1978; U.S. Pat. No. 3,736,668, Dillarstone, issued Jun. 5, 1973; U.S. Pat. No. 3,701,202, Compa et al., issued Oct. 31, 1972; U.S. Pat. No. 3,634,947, Furgal, issued Jan. 18, 1972; U.S. Pat. No. 3,633,538, Hoeflin, issued Jan.

11, 1972; and U.S. Pat. No. 3,435,537, Rumsey, issued Apr. 1, 1969. All of these patents are incorporated herein by reference.

Highly preferred paper, woven or nonwoven "absorbent" substrates useful herein are fully disclosed in U.S. Pat. No. 3,686,025, Morton, issued Aug. 22, 1972, incorporated herein by reference. It is known that most substances are able to absorb a liquid substance to some degree; however, the term "absorbent" as used herein, is intended to mean a substance with an absorbent capacity (i.e., a parameter representing a substrate's ability to take up and retain a liquid) from 4 to 12, preferably 5 to 7, times its weight of water.

(3) Usage

The substrate embodiment of this invention can be used for imparting the above-described fabric treatment composition to fabric to provide perfume effects and/or softening and/or anti-static effects to fabric in an automatic laundry dryer comprises: commingling pieces of damp fabric by tumbling said fabric under heat in an automatic clothes dryer with an effective amount of the fabric treatment composition, at least the continuous phase of said composition having a melting point greater than about 35° C. and said composition being mobilized, e.g., flowable, at dryer operating temperature, said composition comprising from about 0.5% to about 60%, preferably from about 1% to about 50%, more preferably from about 5% to about 40%, of perfume/cyclodextrin complex and from about 30% to about 99%, preferably from about 40% to about 90%, of fabric softening agent selected from the above-defined cationic and nonionic fabric softeners and mixtures thereof.

B. Detergent-Compatible Compositions

Another type of fabric conditioning composition useful herein is detergent-compatible and includes compositions containing softening particles such as those known in the art, including specifically: U.S. Pat. No. 3,936,537, Baskerville Jr., issued Feb. 3, 1976, and U.S. Pat. No. 4,095,946, Jones, issued Jun. 20, 1978, both of which teach the use of intimate mixtures of organic dispersion inhibitors (e.g., stearyl alcohol and fatty sorbitan esters) with solid fabric softener to improve the survival of the softener in the presence of detergent in the washer so that the softener can act on the fabrics when it is mobilized in the dryer, and U.S. Pat. No. 4,234,627, Schilling, issued Nov. 18, 1980, which teaches microencapsulation of fabric softener (The microcapsules survive the wash and adhere to the fabric surface. They are then ruptured by subsequent tumbling of the fabric in the dryer, thereby releasing softener to the fabrics.)

The particles in such detergent-compatible fabric conditioning compositions comprise at least about 10% of fabric softening agent, preferably cationic fabric softening agent. For detergent compatibility, the particles often have a coating as described hereinafter, a sufficiently large particle size (e.g., a minimum dimension greater than about 5,000 microns), or some combination of coating and particle size depending upon the level of protection desired.

The perfume/cyclodextrin complexes are desirably incorporated into fabric conditioning compositions, especially when the compositions are to be added to laundry detergents. It is believed that when the perfume/cyclodextrin complexes are encapsulated in fabric softener, they are attached to the fabric in the laundry dryer.

C. Optional Ingredients

Well known optional components included in fabric conditioning compositions are narrated in U.S. Pat. No. 4,103,047, Zaki et al., issued Jul. 25, 1978, for "Fabric Treatment Compositions," incorporated herein by reference.

6. COMPOSITION SUMMARY

The particulate compositions of the invention can be used in all products in which particulate compositions of the prior art have been used, such as foods, beverages, cosmetics, paper products, detergents, chemical specialties and the like.

The following is a partial list of compositions (applications) for both complexed flavors, fragrances, and other miscellaneous chemicals.

(1) Fragrance

Cosmetics:
Facial scrubs, body powders, lipstick, depilatory powders.
Toiletries:
Dusting powders, bath oils, body oils, bubble bath powders, bath salts.
Personal Care:
Antiperspirants, body sprays, foot sprays, hygiene sprays (all aerosol and nonaerosol), baby diaper sprays, dry shampoos, deodorant body powders, feminine napkin sprays, undergarment sprays (for girdles, etc.), mouthwashes.
Household Products:
Powdered detergents, powdered soaps, room deodorants.
Paper Products:
Disposable baby diapers, disposable bed linens, feminine napkins, tampons, shoe liner inserts, end papers (for use with cold wave lotions and dyes), paper towels, tissues, carbonless carbon paper, typewriter ribbon (ink, with or without fragrance).

(2) Flavors

Snack Foods:
Extruded, cooked, baked, etc.
Desserts:
Canned, mixes, etc., including frozen desserts, e.g., ice cream.
Baked Products:
Cake mixes, cookies, dough, etc.
Seasonings and Garnishings, Synthetic Food Analogs:
Spices, dry mixes and concentrates, etc., that are designed to be added to food either by incorporation or by applying to the surface.
Pet Foods:
Canned, dry, intermediate moisture.
Dry Mixes:
Drink or beverage mixes (instant coffee, teas and/or juices, etc.), soups mixes, sauce and/or salad dressing mixes.

(3) Miscellaneous Chemicals

Incense, room deodorant blocks, solvents, fuels, monomers, lubricants, catalysts, inks, detergents, explosives, drilling fluids, dyes, bacteriocides, fungicides, pesticides, insecticides, insect repellents, pheromones, waxes, and the like.

Additional disclosures of uses can be found in "Cyclodextrins and Their Industrial Uses," Chapter 8, C. Vaution et al., edited by Dominique Duchene and published by Editions de Sante, Paris, 1987, said book and chapter being incorporated herein by reference.

A preferred additional ingredient in the compositions herein is free active, e.g., perfume and/or flavor aroma, other than the active which is present as the active/cyclodextrin complex, which is also very useful for imparting the active, e.g., odor benefits. Such uncomplexed active is preferably present at a level of from about 0.10% to about 10% by weight of the total.

For example, perfume delivery both via free perfume and cyclodextrin/perfume complexes, in solid, dryer-activated, fabric conditioning compositions in laundry fabric dryers is desirable in two ways. Product malodors can be covered by the addition of free perfume to the softener composition to obtain a more preferred product odor, and complexed perfume can be transferred onto fabric with the softener actives in the laundry fabric dryer to provide better in-wear fabric odor. (Preferably, such uncomplexed perfume comprises at least about 1%, more preferably at least about 10% by weight of said uncomplexed perfume, of substantive perfume materials.)

Products of this invention preferably only contain enough free perfume to deliver both an acceptably low product perfume odor and an acceptable initial fabric perfume odor. Perfume incorporated into the product in the form of perfume/CD complex as part of a substrate article or in the form of solid fabric softener particles containing perfume/CD complex (in the case of detergent compatible products), will be released when the fabric is used in situations where renewed perfume odor is really and appropriately needed, e.g., when some moisture is present, such as when using wash cloths and towels in a bathroom, or when there is perspiration odor on clothes during and after a high level of physical activity.

Laundry products can also contain only the perfume/CD complex, without any noticeable amount of free perfume. In this case, the products function initially almost as unscented products.

If a product contains both free and complexed perfume, the escaped perfume from the complex contributes to the overall perfume odor intensity, giving rise to a longer lasting perfume odor impression.

Thus, by adjusting the levels of free perfume and perfume/CD complex it is possible to provide a wide range of unique perfume profiles in terms of timing (release) and/or perfume identity (character). Solid, dryer-activated fabric conditioning compositions are a uniquely desirable way to apply the complexes, since they are applied at the very end of a fabric treatment regimen when the fabric is clean and when there are almost no additional treatments that can affect the perfume.

In addition, the perfume or flavor oils may contain ingredients soluble or suspended in them such as are used in cosmetics, foods, pharmaceuticals and biocidal compositions, e.g., dyes, pigments, vitamins, preservatives, drugs, fungicides, insecticides, bacteriocides, herbicides, and the like.

All percentages, ratios, and parts herein, in the Specification, Examples, and Claims, are by weight unless otherwise stated.

The following are nonlimiting examples of the instant articles and methods.

Four different perfumes used in the following Examples are as follows:

| Substantive Perfume (A) | | Relatively Nonsubstantive Perfume (B) | |
|---|---|---|---|
| Component | Wt. % | Component | Wt. % |
| Benzyl Acetate | 5.0 | Alpha Pinene | 5.0 |
| Benzyl Salicylate | 10.0 | Cedarwood Terpenes | 20.0 |
| Coumarin | 5.0 | Dihydro Myrcenol | 10.0 |
| Ethyl Maltol | 5.0 | Eugenol | 5.0 |
| Ethylene Brassylate | 10.0 | Lavandin | 15.0 |
| Galaxolide ® (50%) | 15.0 | Lemon Oil CP | 10.0 |
| Hexyl Cinnamic Aldehyde | 20.0 | Orange Terpenes | 15.0 |
| | | Phenyl Ethyl Alcohol | 20.0 |
| Gamma Methyl Ionone | 10.0 | Total | 100.0 |
| Lilial ® | 15.0 | | |
| Patchouli | 5.0 | | |
| Total | 100.0 | | |

Complete Perfume (C)

Perfume C is a substantive perfume which is composed mainly of moderate and nonvolatile perfume ingredients. The major ingredients of Perfume C are benzyl salicylate, para-tertiary-butyl cyclohexyl acetate, para-tertiary-butyl-alpha-methyl hydrocinnamic aldehyde, citronellol, coumarin, galaxolide, heliotropine, hexyl cinnamic aldehyde, 4-(4-hydroxy-4-methyl pentyl)-3-cyclohexene-10-carboxaldehyde, methyl cedrylone, gamma-methyl ionone, and patchouli alcohol.

Perfume (D) (More Volatile Portion of Perfume C)

Perfume D is a rather nonsubstantive perfume which is composed mainly of highly and moderately volatile fractions of Perfume C. The major ingredients of Perfume D are linalool, alpha terpineol, citronellol, linalyl acetate, geraniol, hydroxycitronellal, terpinyl acetate, eugenol, and flor acetate. The above-defined perfumes and ethers, as defined hereinafter, are used to form the following complexes, which are used in the Examples herein.

Complex 1—Perfume C/β-CD

A mobile slurry is prepared by mixing about 1 kg of β-CD and 1,000 ml of water in a stainless steel mixing bowl of a KitchenAid mixer using a plastic coated heavy-duty mixing blade. Mixing is continued while about 176 g of Perfume C is slowly added. The liquid-like slurry immediately starts to thicken and becomes a creamy paste. Stirring is continued for about 30 minutes. The paste is now dough-like in appearance. About 500 ml of water is added to the paste and blended well. Stirring is then resumed for an additional approximately 30 minutes. During this time the complex again thickens, although not to the same degree as before the additional water is added. The resulting creamy complex is freeze-dried to produce about 1100 g of powdery solid. Particle size distribution, including agglomerates, determined by the Malvern Particle and Droplet Sizer, Model 2600C, shows that 92% of the complex powder has a size of about 11.1 microns, or less, and 68% of the complex powder has a particle size of about 5.3 microns, or less. Examination of the complex particles by scanning electron microscopy shows that practically all of the ultimate (primary) particles of the complex have particle sizes less than about 5 microns.

Complex 2

Complex 2 is made in a process similar to that of Complex 1, except that the said creamy complex is spread in a thin layer on a tray and allowed to air dry, followed by freeze drying and grinding.

Complex 3

Perfume D/β-CD complex as prepared by the process of Complex 1.

Complex 4

Perfume D/β-CD complex as prepared by the process of Complex 2.

Complex 5

Perfume A/β-CD complex as prepared by the process of Complex 2.

Complex 6

Perfume B/β-CD complex as prepared by the process of Complex 2.

Complex 7

Perfume C is complexed with gamma-CD by the process of Complex 1.

Examples of Fabric Conditioning Substrate Articles

The following compositions are used in Examples 1 and 2:

| Components | Example 1 | Example 2 |
| --- | --- | --- |
| Ditallowdimethylammonium chloride (DTDMAC) | 90.00 | 71.00 |
| Calcium bentonite clay | 5.00 | 4.00 |
| Complex 1 | 5.00 | — |
| Complex 2 | — | 25.00 |
| Totals | 100.00 | 100.00 |

EXAMPLE 1

Preparation of the Coating Mix

An approximately 200 gram batch of the coating mix is prepared as follows. An amount of about 180 g of ditallowdimethylammonium chloride (DTDMAC) is melted at 80° C. The calcium bentonite clay (about 10 g of Bentolite L, available from Southern Clay Co.) is slowly added to the mixture with high shear mixing. During the mixing, the mixture is kept molten in a boiling water bath. The Complex 1 (about 10 g, perfume C/β-CD complex) is then slowly added to the mixture with high shear mixing, and the formula is mixed until the mixture is smooth and homogenous.

Preparation of Fabric Conditioning Sheets

The coating mixture is applied to preweighed nonwoven substrate sheets of about 9 inch×11 inch (approximately 23 cm×28 cm) dimensions. The substrate sheets are comprised of 70% 3-denier, 1 9/16 inch (approximately 4 cm) long rayon fibers with 30% polyvinyl acetate binder. The substrate weight is about 16 g per square yard (about 1.22 g/sheet). A small amount of formula is placed on a heated metal plate with a spatula and then is spread evenly with a wire metal rod. A nonwoven sheet is placed on the metal plate to absorb the coating mixture. The sheet is then removed from the heated metal plate and allowed to cool to room temperature so that the coating mix can solidify. The sheet is weighed to determine the amount of coating mixture on the sheet. The target coating is 2.0 g per sheet. If the weight is in excess of the target weight, the sheet is placed back on the heated metal plate to remelt the coating mixture and remove some of the excess. If the weight is under the target weight, the sheet is also placed on the heated metal plate and more coating mixture is added.

EXAMPLE 2

The coating mix preparation and the making of the fabric conditioning sheets are similar to those in Example 1, except that Complex 2 is used instead of Complex 1.

Fabric Treatment

A laundry load is washed in a washer with the unscented TIDE® detergent. The wet laundry load is transferred and dried in an electric tumble dryer with a fabric conditioning sheet of Example 1 or Example 2 above. The resulting dry fabric has only very low perfume odor, but when the fabric is re-wetted a noticeably stronger perfume odor is obtained.

| Components | Example 3 |
| --- | --- |
| Octadecyldimethylamine | 11.89 |
| $C_{12-14}$ fatty acid | 8.29 |
| $C_{16-18}$ fatty acid | 10.69 |
| DTDMAMS | 19.32 |
| Sorbitan monostearate | 19.32 |
| Clay | 3.86 |
| Complex 2 | 26.62 |
| Totals | 100.00 |
| Coating Wt. per Sheet (g) | 2.33 |

EXAMPLE 3

A first blend of about: 11.89 parts octadecyldimethylamine (Ethyl Corporation); 8.29 parts $C_{12-14}$ fatty acid (The Procter & Gamble Co.); and 10.69 parts $C_{16-18}$ fatty acid (Emery Industries, Inc.) are melted together at 80° C., and a second blend of about 19.32 parts sorbitan monostearate (Mazer Chemicals, Inc.) and 19.32 parts ditallowdimethylammonium methyl sulfate, DTDMAMS, (Sherex Chemical Co.) are melted together to form the softener component of the composition, during which time the mixture is kept molten in a boiling water bath. The calcium bentonite clay (3.86 parts Bentolite L, available from Southern Clay Co.) is then slowly added to the mixture while high shear mixing. An amount of about 26.62 parts of Complex 2 (inclusion complex of Perfume C in β-cyclodextrin) is then added in small portions and the formula is mixed until the mixture is smooth and completely homogenous.

The coating mixture is applied to preweighed nonwoven substrate sheets as in Example 1. The target coating is 2.33 g per sheet. Each sheet contains about 1.62 g of softener, about 0.09 g of clay, and about 0.62 g of Complex 2.

| Components | Example 4 | Example 5 |
| --- | --- | --- |
| Octadecyldimethylamine | 10.88 | 11.63 |
| $C_{12-14}$ fatty acid | 7.58 | — |
| $C_{16-18}$ fatty acid | 9.78 | 20.59 |
| DTDMAMS | 17.67 | 20.20 |
| Sorbitan monostearate | 17.67 | 20.20 |
| Clay | 3.54 | 5.99 |
| Complex 3 | 30.44 | 18.93 |
| Free Perfume C | 2.44 | 2.46 |
| Totals | 100.00 | 100.00 |
| Coating Wt. per Sheet (g) | 2.55 | 2.52 |

EXAMPLE 4

The softener mixture of Example 4 is prepared similarly to that of Example 3. However, the coating mixture of Example 4 contains both Perfume C in the free state and Perfume D complexed with the β-CD (Complex 3). The free Perfume C provides the initial perfume odor to the dry fabrics, while the complexed Perfume D is used to provide the freshness impression to the re-wetted fabrics. The target coating is 2.55 g per sheet. Each sheet contains about 1.62 g of softener, about 0.09 g of clay, about 0.78 g of Complex 3, and about 0.062 g of free Perfume C.

EXAMPLE 5

A dryer-added fabric conditioning article comprising a rayon nonwoven fabric substrate [having a weight of 1.22 g per 99 sq. in. (approximately 639 cm$^2$)] and a fabric conditioning composition is prepared in the following manner.

A premixture is prepared by admixing 11.63 parts octadecyldimethylamine with about 20.59 parts $C_{16-18}$ fatty acid at about 75° C. Then about 20.20 parts sorbitan monostearate and 20.20 parts ditallowdimethylammonium methylsulfate are added with high shear mixing at about 75° C. After the addition is completed and a sufficient period of mixing time has elapsed, about 5.99 parts of Bentolite L particulate clay is added slowly while maintaining the high shear mixing action. Then about 18.93 parts of Complex 3 are added with mixing. Finally about 2.46 parts of free Perfume C is added to complete the preparation of the fabric conditioning composition.

The flexible substrate, comprised of 70% 3-denier, 1%6 inch long (approximately 4 cm) rayon fibers and 30% polyvinyl acetate binder, is impregnated by coating one side of a continuous length of the substrate and contacting it with a rotating cylindrical member which serves to press the liquified mixture into the interstices of the substrate. The amount of fabric conditioning mixture applied is controlled by the flow rate of the mixture and/or the line speed of the substrate. The substrate is passed over several chilled tension rolls which help solidify the conditioning mixture. The substrate sheet is 9 inches wide (approximately 23 cm) and is perforated in lines at 11 inch intervals (approximately 28 cm) to provide detachable sheets. Each sheet is cut with a set of knives to provide three evenly spaced parallel slits averaging about 4 inches in length (approximately 10 cm). In this Example 5, the application rate is adjusted to apply about 2.52 g of coating mixture per sheet. Each sheet contains about 1.83 g of softener, about 0.15 g of clay, about 0.48 g of Complex 3, and about 0.062 g of free Perfume C.

| Components | Example 6 | Example 7 | Example 8 |
|---|---|---|---|
| Octadecyldimethylamine | 10.85 | 10.85 | 10.85 |
| $C_{16-18}$ fatty acid | 19.21 | 19.21 | 19.21 |
| DTDMAMS | 18.85 | 18.85 | 18.85 |
| Sorbitan monostearate | 18.85 | 18.85 | 18.85 |
| Clay | 4.50 | 4.50 | 4.50 |
| Complex 5 | 27.74 | — | — |
| Complex 6 | — | 27.74 | — |
| Complex 7 | — | — | 27.74 |
| Totals | 100.00 | 100.00 | 100.00 |
| Coating Wt. per Sheet (g) | 2.45 | 2.45 | 2.45 |

EXAMPLES 6–8

Fabric conditioning sheets of Examples 6 to 8 are prepared by the same procedure as that of Example 3. The target coating weight is 2.45 g per sheet.

Fabrics treated with any of the above sheets in the tumble dryer will emit extra fragrance odor when the fabrics are rewetted with water or perspiration.

Examples of Detergent-Compatible Particles

EXAMPLE 9

| Softener Core Particles | |
|---|---|
| Components | Example 9 |
| Ditallowdimethylammonium methylsulfate (DTDMAMS) | 38.51 |
| Cetyl Alcohol | 19.17 |
| Sorbitan Monostearate | 19.17 |
| Complex 1 | 20.15 |
| Calcium Bentonite Clay | 3.00 |
| Total | 100.00 |

The DTDMAMS, cetyl alcohol and sorbitan monostearate are blended together in a PVM 40 Ross mixer (Charles Ross & Sons Company, Hauppauge, N.Y. 11788) at about 71° C. The molten "triblend" is then mixed for one hour. At the end of one hour, the temperature is raised to 79°–85° C. under vacuum (about 330–430 mm Hg). When the temperature has stabilized in this range, the Ross anchor and disperser are turned on and the Complex 1 and the clay are added, the mixture is blended for 5 minutes and then sheared with the Ross colloid mixer for 10 minutes. The softener composition is then poured into trays and cooled overnight at about 4° C. Particles are formed by cooling and then milling in a Fitzmill, Model DA506 (The Fitzpatrick Company, Elmhurst, Ill. 60126) at 4740 rpm's through a 4 mesh screen. The particles are then sized through 11 on 26 (U.S. Standard screens, (0.6–1.7 mm) particle size).

The particles are then coated with a 10% solution of Ethocel in methanol. The coating is applied in an 18 inch Wurster Coater (Coating Place, Inc., P.O. Box 248, Verona, Wis. 53593). The ethyl cellulose used is Ethocel Std. 10 (Dow Chemical Co., Midland, Mich. 48640), which has an Ubbelohde viscosity of 9.0–11.0, measured at 25° C. as a 5% solution in 80% toluene/20% ethanol.

The following conditions are used to apply the cellulose-based coating:

| | |
|---|---|
| Fluidizing Air | 15.8 Cu. M/min. at 40.5° C. |
| Atomizing Air Volume | 0.37 Cu. M/min. |
| Atomizing Air Rate | 5624 g/sq. cm. |
| Inlet Air Temperature | 38° C.–43° C. |
| Outlet Air Temperature | 30° C.–32° C. |
| Pump Rate | 0.2 Kg/min. |
| Nozzle Size | CPI-18-A74* |
| Partition Gap | 216 mm × 267 mm |
| Partition Size | 19 mm |
| Run Time | 55 min. |

*Available from Coating Place, Inc.

The amount of coating applied to the particles is about 3% by weight of the total coated particle weight. When the coating is completed, the softener particles are resized through 11 on 26 mesh U.S. Standard screens and are then ready for use "as is" or for blending into detergent granules.

EXAMPLE 10

A detergent/softener composition is prepared by mixing about 5.2 parts of the coated softener particles of Example 9 with 94.8 parts of the following granular detergent composition:

| Ingredient | Parts |
| --- | --- |
| Na C$_{13}$ linear alkyl benzene sulfonate | 9.5 |
| Na C$_{14-15}$ fatty alcohol sulfate | 9.5 |
| Ethoxylated C$_{12-13}$ fatty alcohol | 1.9 |
| Na$_2$SO$_4$ | 11.1 |
| Sodium silicate (1.6r) | 6.5 |
| Polyethylene glycol (M.W. 8,000) | 0.7 |
| Polyacrylic acid (M.W. 1,200) | 0.9 |
| Sodium tripolyphosphate | 31.0 |
| Sodium pyrophosphate | 7.5 |
| Na$_2$CO$_3$ | 10.2 |
| Optical brightener | 0.2 |
| Protease enzyme (Alcalase) | 0.7 |
| Moisture | 9.3 |
| Miscellaneous | 1.0 |
| Total | 100.0 |

EXAMPLE 11

Alternate granular detergent/softener compositions are prepared by mixing about 5.2 parts of the coated softener of Example 9 with about 94.8 parts of the following granular detergent composition:

| Ingredient | Parts |
| --- | --- |
| Na C$_{13}$ linear alkyl benzene sulfonate | 11.5 |
| Na C$_{14-15}$ fatty alcohol sulfate | 11.5 |
| Ethoxylated C$_{12-13}$ fatty alcohol | 1.9 |
| Na$_2$SO$_4$ | 14.0 |
| Sodium silicate (1.6r) | 2.3 |
| Polyethylene glycol (M.W. 8,000) | 1.8 |
| Polyacrylic acid (M.W. 1,200) | 3.5 |
| Hydrated Zeolite A (~2 microns) | 28.9 |
| Na$_2$CO$_3$ | 17.0 |
| Optical brightener | 0.2 |
| Protease enzyme (Alcalase) | 0.6 |
| Moisture and Miscellaneous | 7.0 |
| Total | 100.2 |

EXAMPLE 12

A complex of food grade, cold-press, orange oil and beta-cyclodextrin is prepared by a process like that in Complex 1. The resulting small particle size complex is admixed with the commercial product Tang® at a level of about 1% and the resulting dry, powdered, orange flavored mix has a noticeably stronger orange aroma and flavor than the original product when it is mixed with water.

EXAMPLE 13

A complex of peppermint oil and beta-cyclodextrin is prepared by a process like that in Complex 1. The resulting small particle size complex is admixed with chicle at a ratio of about 1 to 100 and then blended with about 300 parts of sucrose and about 100 parts of corn syrup in a ribbon blender. The resulting chewing gum blend is then extruded in strips that are about 2.5 centimeters wide and about 0.25 centimeters thick, cut into lengths that are about 10 centimeters long and stored for about one year. When chewed, the gum provides a strong and long-lasting peppermint flavor.

EXAMPLE 14

A complex of beta-cyclodextrin and coffee oil containing cryogenic condensates of the headspace of roasted coffee bean grinders, is prepared by a process like that in Complex 1. The resulting small particle size complex is admixed at a ratio of about 2 to 100 with instant coffee (Folgers®) and when the coffee is added to water exhibits enhanced coffee aroma as compared to the instant coffee alone.

EXAMPLE 15

Blueberry, raspberry, mint, orange, and lemon flavor oil extracts are each complexed with beta-cyclodextrin in processes like that in Complex 1 and each of the resulting small particle size complexes is incorporated into both muffin and white cake mixes at a level of about 1%. Batters and baked goods prepared with the mixes have enhanced flavor profiles.

EXAMPLE 16

The flavor complexes of Example 15 are mixed with sucrose at a level of about 1% to make instant drink mixes. When the mixes are used to prepare drinks by adding water, the drinks have the indicated flavors.

EXAMPLE 17

A beef fat extract and a chicken fat extract are each complexed with beta-cyclodextrin in processes like that in Complex 1. The resulting complexes are each mixed with instant rice at a level of about 4% to form soup mixes that provide soups with improved flavor when they are mixed with hot water.

EXAMPLE 18

A mixture of plant flavor oils comprising celery oil, garlic oil, and bay leaf oil in approximately equal amounts is complexed with beta-cyclodextrin in a process like that in Complex 1. The resulting small particle complex is mixed with salt in a roughly 3:1 ratio to provide a mix that, when admixed with sour cream, is useful as a dip or salad dressing.

EXAMPLE 19

An extract of jalapeno peppers is complexed with beta-cyclodextrin in a process like that in Complex 1. The resulting small particle size complex is admixed with paprika in a ratio of about 1:100. The resulting powder, when applied to the surface of foods, provides a strong pepper effect that is roughly proportional to the color of the surface.

EXAMPLE 20

Butter flavor is complexed with beta-cyclodextrin in a process like that in Complex 1. The resulting small particle size complex can be advantageously mixed with a brownie mix at a level of about 1%; with salt at a ratio of about 1 to 10 for addition to, e.g., popcorn, baked fish, mushrooms, escargot, etc.; and at a level of about 1% to make frozen desserts such as ice cream, frozen yogurt, milk shakes, malts, etc.

What is claimed is:

1. Solid dry consumer composition comprising an effective amount of active/cyclodextrin inclusion complex with pharmaceutical agent, said complex being prepared by the kneading method and having a particle size of less than about 5 microns which provides for fast release of said pharmaceutical agent.

2. The composition of claim 1 wherein said cyclodextrin is selected from the group consisting of: unsubstituted cyclodextrins containing from about six to about twelve glucose units; derivatives of said unsubstituted cyclodextrins; and mixtures thereof, and wherein said cyclodextrin is capable of forming inclusion complexes with said pharmaceutical agent.

3. The composition of claim 2 wherein at least a major portion of said cyclodextrin is selected from the group consisting of alpha-cyclodextrin; beta-cyclodextrin; gamma-cyclodextrin; and mixtures thereof.

4. The composition of claim 2 wherein at least a major portion of said cyclodextrin is beta-cyclodextrin.

* * * * *